United States Patent
Gregory et al.

(10) Patent No.: US 9,720,480 B2
(45) Date of Patent: *Aug. 1, 2017

(54) PORTABLE COMPUTING DEVICE AND METHOD FOR ASSET MANAGEMENT IN A LOGISTICS SYSTEM

(71) Applicant: FedEx Corporate Services, Inc., Collierville, TN (US)

(72) Inventors: Timothy L. Gregory, Collierville, TN (US); Andy N. Lemmon, Tuscaloosa, AL (US); John Marshall Veitenheimer, Arlington, TN (US); James Randy Jacobs, Murfreesboro, TN (US); Miley E. Ainsworth, Hernando, MS (US)

(73) Assignee: FedEx Corporate Services, Inc., Collierville, TN (US)

( * ) Notice: Subject to any disclaimer, the term of this patent is extended or adjusted under 35 U.S.C. 154(b) by 41 days.

This patent is subject to a terminal disclaimer.

(21) Appl. No.: 14/638,577

(22) Filed: Mar. 4, 2015

(65) Prior Publication Data

US 2015/0177810 A1    Jun. 25, 2015

Related U.S. Application Data

(63) Continuation of application No. 13/738,117, filed on Jan. 10, 2013, now Pat. No. 9,002,679, which is a
(Continued)

(51) Int. Cl.
*G06F 1/32* (2006.01)
*G06Q 10/08* (2012.01)
(Continued)

(52) U.S. Cl.
CPC .......... *G06F 1/3206* (2013.01); *G01D 9/005* (2013.01); *G01N 21/00* (2013.01); *G06F 1/3287* (2013.01);
(Continued)

(58) Field of Classification Search
CPC .......... E06B 9/42; G01D 9/005; G01N 21/00; G06F 1/3206; G06F 1/3287; G06Q 10/0833

See application file for complete search history.

(56) References Cited

U.S. PATENT DOCUMENTS

| 5,223,844 A | 6/1993 | Mansell et al. |
| 5,347,274 A | 9/1994 | Hassett |

(Continued)

FOREIGN PATENT DOCUMENTS

| EP | 1 037 447 | 9/2000 |
| EP | 1189163 | 3/2002 |

(Continued)

OTHER PUBLICATIONS

CrossCheck™ AMPS with IQ Event Engine™ Firmware Operation Manual, Trimble Navigation Limited, Nov. 1998.

(Continued)

*Primary Examiner* — Yong Hang Jiang
(74) *Attorney, Agent, or Firm* — Finnegan, Henderson, Farabow, Garrett & Dunner, L.L.P.

(57) ABSTRACT

Systems, methods, and computer program products are provided for tracking one or more items. In one exemplary embodiment, there is provided a device for tracking one or more items. The device may include a plurality of sensors for detecting light, temperature, humidity, pressure, and acceleration. The device may also include a memory for storing information received from the plurality of sensors.

20 Claims, 7 Drawing Sheets

Related U.S. Application Data continuation of application No. 13/565,738, filed on Aug. 2, 2012, now Pat. No. 8,560,274, which is a continuation of application No. 12/566,876, filed on Sep. 25, 2009, now Pat. No. 8,239,169.

(51) Int. Cl.
   *G01D 9/00* (2006.01)
   *G01N 21/00* (2006.01)

(52) U.S. Cl.
   CPC ......... *G06Q 10/08* (2013.01); *G06Q 10/0833* (2013.01)

(56) References Cited

U.S. PATENT DOCUMENTS

| | | |
|---|---|---|
| 5,389,934 A | 2/1995 | Kass |
| 5,400,020 A | 3/1995 | Jones et al. |
| 5,461,365 A | 10/1995 | Schlager et al. |
| 5,491,486 A | 2/1996 | Welles, II et al. |
| 5,512,902 A | 4/1996 | Guthrie et al. |
| 5,515,858 A | 5/1996 | Myllymaki |
| 5,528,247 A | 6/1996 | Nonami |
| 5,539,748 A | 7/1996 | Raith |
| 5,541,845 A | 7/1996 | Klein |
| 5,550,551 A | 8/1996 | Alesio |
| 5,568,119 A | 10/1996 | Schipper |
| 5,570,412 A | 10/1996 | LeBlanc |
| 5,576,716 A | 11/1996 | Sadler |
| 5,588,005 A | 12/1996 | Ali et al. |
| 5,592,173 A | 1/1997 | Lau et al. |
| 5,608,412 A | 3/1997 | Welles, II et al. |
| 5,623,260 A | 4/1997 | Jones |
| 5,627,517 A | 5/1997 | Theimer et al. |
| 5,629,678 A | 5/1997 | Gargano et al. |
| 5,631,827 A | 5/1997 | Nicholls et al. |
| 5,648,770 A | 7/1997 | Ross |
| 5,652,570 A | 7/1997 | Lepkofker |
| 5,686,888 A | 11/1997 | Welles, II et al. |
| 5,691,980 A | 11/1997 | Welles, II et al. |
| 5,710,551 A | 1/1998 | Ridgeway |
| 5,712,619 A | 1/1998 | Simkin |
| 5,731,757 A | 3/1998 | Layson, Jr. |
| 5,742,233 A | 4/1998 | Hoffman et al. |
| 5,751,245 A | 5/1998 | Janky et al. |
| 5,771,001 A | 6/1998 | Cobb |
| 5,771,455 A | 6/1998 | Kennedy, III et al. |
| 5,774,876 A | 6/1998 | Woolley et al. |
| 5,797,091 A | 8/1998 | Clise et al. |
| RE35,920 E | 10/1998 | Sorden et al. |
| 5,826,195 A | 10/1998 | Westerlage et al. |
| 5,835,907 A | 11/1998 | Newman |
| 5,841,352 A | 11/1998 | Prakash |
| 5,844,862 A | 12/1998 | Cocatre-Zilgien |
| 5,850,196 A | 12/1998 | Mowers |
| 5,869,819 A | 2/1999 | Knowles et al. |
| 5,889,770 A | 3/1999 | Jokiaho et al. |
| 5,892,441 A | 4/1999 | Woolley et al. |
| 5,917,433 A | 6/1999 | Keillor et al. |
| 5,948,043 A | 9/1999 | Mathis |
| 5,959,575 A | 9/1999 | Abbott |
| 5,963,130 A | 10/1999 | Schlager et al. |
| 6,002,363 A | 12/1999 | Krasner |
| 6,002,982 A | 12/1999 | Fry |
| 6,009,319 A | 12/1999 | Khullar et al. |
| 6,013,007 A | 1/2000 | Root et al. |
| 6,014,080 A | 1/2000 | Layson, Jr. |
| 6,014,090 A | 1/2000 | Rosen et al. |
| 6,023,241 A | 2/2000 | Clapper |
| 6,032,051 A | 2/2000 | Hall et al. |
| 6,034,622 A | 3/2000 | Levine |
| 6,054,928 A | 4/2000 | Lemelson et al. |
| 6,064,336 A | 5/2000 | Krasner |
| 6,067,044 A | 5/2000 | Whelan et al. |
| 6,072,396 A | 6/2000 | Gaukel |
| 6,078,290 A | 6/2000 | McBurney et al. |
| 6,083,248 A | 7/2000 | Thompson |
| 6,083,353 A | 7/2000 | Alexander, Jr. |
| 6,094,168 A | 7/2000 | Duffett-Smith et al. |
| 6,094,642 A | 7/2000 | Stephenson et al. |
| 6,121,922 A | 9/2000 | Mohan |
| 6,131,067 A | 10/2000 | Girerd et al. |
| 6,141,570 A | 10/2000 | O'Neill, Jr. et al. |
| 6,144,303 A | 11/2000 | Federman |
| 6,148,280 A | 11/2000 | Kramer |
| 6,163,696 A | 12/2000 | Bi et al. |
| 6,171,264 B1 | 1/2001 | Bader |
| 6,172,640 B1 | 1/2001 | Durst et al. |
| 6,175,616 B1 | 1/2001 | Light et al. |
| 6,198,390 B1 | 3/2001 | Schlager et al. |
| 6,198,431 B1 | 3/2001 | Gibson |
| 6,198,930 B1 | 3/2001 | Schipper |
| 6,199,045 B1 | 3/2001 | Giniger et al. |
| 6,220,509 B1 | 4/2001 | Byford |
| 6,226,622 B1 | 5/2001 | Dabbiere |
| 6,231,519 B1 | 5/2001 | Blants et al. |
| 6,232,916 B1 | 5/2001 | Grillo et al. |
| 6,236,358 B1 | 5/2001 | Durst et al. |
| 6,238,337 B1 | 5/2001 | Kambhatla et al. |
| 6,243,039 B1 | 6/2001 | Elliot |
| 6,243,660 B1 | 6/2001 | Hsu et al. |
| 6,246,376 B1 | 6/2001 | Bork et al. |
| 6,255,942 B1 | 7/2001 | Knudsen |
| 6,263,280 B1 | 7/2001 | Stingone, Jr. |
| 6,278,936 B1 | 8/2001 | Jones |
| 6,281,797 B1 | 8/2001 | Forster et al. |
| 6,292,687 B1 | 9/2001 | Lowell et al. |
| 6,292,724 B1 | 9/2001 | Apsell et al. |
| 6,292,784 B1 | 9/2001 | Martin et al. |
| 6,298,306 B1 | 10/2001 | Suarez et al. |
| 6,300,875 B1 | 10/2001 | Schafer |
| 6,304,856 B1 | 10/2001 | Soga et al. |
| 6,314,308 B1 | 11/2001 | Sheynblat et al. |
| 6,317,049 B1 | 11/2001 | Toubia et al. |
| 6,323,807 B1 | 11/2001 | Golding et al. |
| 6,324,213 B1 | 11/2001 | Harrison |
| 6,327,533 B1 | 12/2001 | Chou |
| 6,331,817 B1 | 12/2001 | Goldberg |
| 6,339,397 B1 | 1/2002 | Baker |
| 6,340,928 B1 | 1/2002 | McCurdy |
| 6,349,257 B1 | 2/2002 | Liu et al. |
| 6,353,390 B1 | 3/2002 | Beri et al. |
| 6,353,798 B1 | 3/2002 | Green et al. |
| 6,356,841 B1 | 3/2002 | Hamrick et al. |
| 6,362,778 B2 | 3/2002 | Neher |
| 6,363,254 B1 | 3/2002 | Jones et al. |
| 6,363,323 B1 | 3/2002 | Jones |
| 6,377,810 B1 | 4/2002 | Geiger et al. |
| 6,388,612 B1 | 5/2002 | Neher |
| 6,404,352 B1 | 6/2002 | Ichikawa et al. |
| 6,407,698 B1 | 6/2002 | Ayed |
| 6,411,892 B1 | 6/2002 | van Diggelen |
| 6,411,899 B2 | 6/2002 | Dussell et al. |
| 6,421,538 B1 | 7/2002 | Byrne |
| 6,426,719 B1 | 7/2002 | Nagareda et al. |
| 6,427,120 B1 | 7/2002 | Garin et al. |
| 6,429,810 B1 | 8/2002 | De Roche |
| 6,430,602 B1 | 8/2002 | Kay et al. |
| 6,433,732 B1 | 8/2002 | Dutta et al. |
| 6,435,018 B1 | 8/2002 | Murakami et al. |
| 6,441,778 B1 | 8/2002 | Durst et al. |
| 6,442,380 B1 | 8/2002 | Mohindra |
| 6,445,937 B1 | 9/2002 | daSilva |
| 6,452,572 B1 | 9/2002 | Fan et al. |
| 6,453,237 B1 | 9/2002 | Fuchs et al. |
| 6,459,365 B2 | 10/2002 | Tamura |
| 6,463,272 B1 | 10/2002 | Wallace et al. |
| 6,463,420 B1 | 10/2002 | Guidice et al. |
| 6,469,639 B2 | 10/2002 | Tanenhaus et al. |
| 6,471,087 B1 | 10/2002 | Shusterman |
| 6,478,736 B1 | 11/2002 | Mault |
| 6,480,108 B2 | 11/2002 | McDonald |
| 6,484,079 B2 | 11/2002 | Buckelew et al. |
| 6,496,695 B1 | 12/2002 | Kouji et al. |

(56) References Cited

U.S. PATENT DOCUMENTS

| | | |
|---|---|---|
| 6,496,775 B2 | 12/2002 | McDonald, Jr. et al. |
| 6,496,777 B2 | 12/2002 | Tennison et al. |
| 6,512,478 B1 | 1/2003 | Chien |
| 6,513,532 B2 | 2/2003 | Mault et al. |
| 6,522,871 B1 | 2/2003 | Patrick et al. |
| 6,522,889 B1 | 2/2003 | Aarnio |
| 6,529,164 B1 | 3/2003 | Carter |
| 6,544,193 B2 | 4/2003 | Abreu |
| 6,552,652 B2 | 4/2003 | Beken |
| 6,559,620 B2 | 5/2003 | Zhou et al. |
| 6,559,802 B2 | 5/2003 | Goto et al. |
| 6,569,094 B2 | 5/2003 | Suzuki et al. |
| 6,579,231 B1 | 6/2003 | Phipps |
| 6,611,755 B1 | 8/2003 | Coffee et al. |
| 6,625,437 B1 | 9/2003 | Jampolsky et al. |
| 6,640,085 B1 | 10/2003 | Chatzipetros et al. |
| 6,650,907 B1 | 11/2003 | Kamperschroer et al. |
| 6,656,125 B2 | 12/2003 | Misczynski et al. |
| 6,721,542 B1 | 4/2004 | Anttila et al. |
| 6,747,675 B1 | 6/2004 | Abbott et al. |
| 6,748,318 B1 | 6/2004 | Jones |
| 6,772,130 B1 | 8/2004 | Karbowski et al. |
| 6,801,850 B1 | 10/2004 | Wolfson |
| 6,804,606 B2 | 10/2004 | Jones |
| 6,812,840 B2 | 11/2004 | Gehlot et al. |
| 6,847,892 B2 | 1/2005 | Zhou et al. |
| 6,856,804 B1 | 2/2005 | Ciotta |
| 6,924,750 B2 | 8/2005 | Flick |
| 6,952,645 B1 | 10/2005 | Jones |
| 6,975,941 B1 | 12/2005 | Lau et al. |
| 6,976,007 B1 | 12/2005 | Boucher et al. |
| 7,002,451 B2 | 2/2006 | Freeman |
| 7,034,683 B2 | 4/2006 | Ghazarian |
| 7,035,856 B1 | 4/2006 | Morimoto |
| 7,113,784 B2 | 9/2006 | Fujiwara et al. |
| 7,174,173 B1 | 2/2007 | Needham et al. |
| 7,183,945 B2 | 2/2007 | DiDomenico et al. |
| 7,187,278 B2 | 3/2007 | Biffar |
| 7,202,801 B2 | 4/2007 | Chou |
| 7,212,829 B1 | 5/2007 | Lau et al. |
| 7,243,080 B2 | 7/2007 | Bhadra |
| 7,253,731 B2 | 8/2007 | Joao |
| 7,258,276 B2 | 8/2007 | Linton et al. |
| 7,512,515 B2 | 3/2009 | Vock et al. |
| 7,552,031 B2 | 6/2009 | Vock et al. |
| 7,627,666 B1 | 12/2009 | DeGiulio et al. |
| 7,791,455 B1 | 9/2010 | MacLean, III et al. |
| 8,019,740 B2 | 9/2011 | Weng et al. |
| 2001/0020204 A1 | 9/2001 | Runyon et al. |
| 2001/0028304 A1 | 10/2001 | I'Anson et al. |
| 2001/0044299 A1 | 11/2001 | Sandegren |
| 2001/0047244 A1 | 11/2001 | Harrison et al. |
| 2001/0052849 A1 | 12/2001 | Jones, Jr. |
| 2002/0000930 A1 | 1/2002 | Crowson et al. |
| 2002/0014955 A1 | 2/2002 | Klitsgaard |
| 2002/0016171 A1 | 2/2002 | Doganata et al. |
| 2002/0027507 A1 | 3/2002 | Yarin et al. |
| 2002/0038182 A1 | 3/2002 | Wong et al. |
| 2002/0050945 A1 | 5/2002 | Tsukishima et al. |
| 2002/0057192 A1 | 5/2002 | Eagleson et al. |
| 2002/0061758 A1 | 5/2002 | Zarlengo et al. |
| 2002/0070856 A1 | 6/2002 | Wolfe |
| 2002/0077080 A1 | 6/2002 | Greene |
| 2002/0087260 A1 | 7/2002 | Hancock et al. |
| 2002/0087619 A1 | 7/2002 | Tripathi |
| 2002/0111171 A1 | 8/2002 | Boesch et al. |
| 2002/0111819 A1 | 8/2002 | Li et al. |
| 2002/0115453 A1 | 8/2002 | Poulin et al. |
| 2002/0119789 A1 | 8/2002 | Friedman |
| 2002/0120475 A1 | 8/2002 | Morimoto |
| 2002/0143670 A1 | 10/2002 | Cushing et al. |
| 2002/0165638 A1 | 11/2002 | Bancroft et al. |
| 2002/0175805 A9 | 11/2002 | Armstrong et al. |
| 2002/0187025 A1 | 12/2002 | Speasl et al. |
| 2002/0193121 A1 | 12/2002 | Nowak et al. |
| 2003/0001742 A1 | 1/2003 | Eshelman et al. |
| 2003/0003943 A1 | 1/2003 | Bajikar |
| 2003/0004403 A1 | 1/2003 | Drinan et al. |
| 2003/0061176 A1 | 3/2003 | Hoar |
| 2003/0069002 A1 | 4/2003 | Hunter et al. |
| 2003/0069759 A1 | 4/2003 | Smith |
| 2003/0084005 A1 | 5/2003 | Wong et al. |
| 2003/0115978 A1 | 6/2003 | Moehnke et al. |
| 2003/0151507 A1 | 8/2003 | Andre et al. |
| 2003/0204452 A1 | 10/2003 | Wheeler |
| 2004/0034470 A1 | 2/2004 | Workman |
| 2004/0046637 A1 | 3/2004 | Wesby Van Swaay |
| 2004/0117108 A1 | 6/2004 | Nemeth |
| 2005/0071258 A1 | 3/2005 | Kumakawa |
| 2005/0171876 A1* | 8/2005 | Golden ............... G06Q 40/12 705/30 |
| 2006/0173444 A1 | 8/2006 | Choy et al. |
| 2006/0187026 A1 | 8/2006 | Kochis |
| 2007/0267509 A1* | 11/2007 | Witty ............... G01D 9/005 236/51 |
| 2007/0290836 A1 | 12/2007 | Ainsworth et al. |
| 2008/0021953 A1 | 1/2008 | Gil |
| 2009/0040043 A1* | 2/2009 | Rohr ............... G01S 5/0027 340/539.13 |
| 2009/0061897 A1* | 3/2009 | Hamilton ............... G06Q 10/08 455/456.2 |
| 2009/0150114 A1 | 6/2009 | Vock et al. |
| 2009/0292682 A1 | 11/2009 | Robbins |
| 2009/0295581 A1 | 12/2009 | Paananen et al. |
| 2010/0332284 A1 | 12/2010 | Hilbush et al. |
| 2012/0199655 A1 | 8/2012 | Fukuba |

FOREIGN PATENT DOCUMENTS

| | | |
|---|---|---|
| GB | 2329491 A | 9/1997 |
| WO | WO 97/41654 | 11/1997 |
| WO | WO 98/01769 | 1/1998 |
| WO | WO 98/16045 | 4/1998 |
| WO | WO 00/51391 | 8/2000 |
| WO | WO 01/50151 | 7/2001 |
| WO | WO 01/65444 | 9/2001 |
| WO | WO 01/75700 | 10/2001 |
| WO | WO 01/97167 | 12/2001 |
| WO | WO 02/42979 | 5/2002 |
| WO | WO 02/084618 | 10/2002 |
| WO | WO 02/101505 | 12/2002 |
| WO | WO 03/012720 | 2/2003 |

OTHER PUBLICATIONS

CrossCheck™ GSM Mobile Unit Operation Manual, Trimble, Jul. 2001.

TAIP/IQEvent Engine Reference, Trimble Navigation Limited, Aug. 1999.

ReZolt Corporate Backgrounder RZCORP-111011, www.ReZolt.com, 2011.

Venable LLP, Homeland Security Alert, Maritime Transportation Security Act of 2002, Dec. 2002.

Frittelli, John F., Port and Maritime Security: Background and Issues for Congress, CRS Report for Congress, Received through the CRS Web, updated May 27, 2005.

Environmental Cyberinfrastructure Needs for Distributed Sensor Networks, A Report From a National Science Foundation Sponsored Workshop, Scripps Institute of Oceanography, Aug. 2003.

Ruiz-Garcia et al.,"Monitoring Cold Chain Logistics by means of RFID," from Sustainable Radio Frequency Identification Solutions, Book edited by Cristina Turcu, Feb. 2010.

Shirley, Donna et al., "Mars Rovers: Past, Present and Future," Princeton Space Studies Institute's 20th Anniversary Conference May 1997.

MICA Wireless Measurement System, Crossbow Technology, Inc., San Jose, CA.

Culler, David et al., "MICA: The Commercialization of Microsensor Motes" | Sensors, Apr. 2002.

Kahn, J.M. et al., "Next Century Challenges: Mobile Networking for 'Smart Dust'."

(56) References Cited

OTHER PUBLICATIONS

Wolfe, Michael, "Electronic Cargo Seals: Context, Technologies, and Marketplace," Jul. 2002.
Maestas, Eli et al., "Demonstration of the Radio Frequency Identification Transportation Security and Safety System," Oct. 15, 2003.
"Remote Sensing for Transportation," Report of a Conference, Washington D.C., Dec. 2000.
Horton, Mike et al., "MICA the Commercialization of Microsensor Motes," Sensor Technology and Design, Apr. 2002.
System Planning Corp. helps evaluate seamless container-security system, The Journal of Commerce, May 2005.
Prasad, Lakshman, et al., Application of Shape Analysis to domestic and international security. Institute of Nuclear Materials Management Conference 2002, Orlando, Florida, Jun. 2002.
Spencer, B.F. et al., "Smart Sensing Technology: Opportunities and Challenges."
Hill, Jason, "A Software Architecture Supporting Networked Sensors" Dept. of Electrical Engineering and Computer Sciences, U.C. Berkeley, Fall 2000.
Kremens, Robert et al., Low Cost Autonomous Field-Deployable Environment Sensors.
Akyildiz, I.F. et al., "Wireless Sensor Networks: a Survey" Computer Networks 38 (2002) 393-422.

\* cited by examiner

PORTABLE COMPUTING DEVICE AND METHOD FOR ASSET MANAGEMENT IN A LOGISTICS SYSTEM

CROSS REFERENCE TO RELATED APPLICATIONS

This is a continuation of U.S. patent application Ser. No. 13/738,117, filed Jan. 10, 2013 (pending), which is a continuation of U.S. patent application Ser. No. 13/565,738, filed Aug. 2, 2012, now U.S. Pat. No. 8,560,274 issued Oct. 15, 2013, which is a continuation of U.S. patent application Ser. No. 12/566,876, filed Sep. 25, 2009, now U.S. Pat. No. 8,239,169 issued on Aug. 7, 2012, all of which are incorporated herein by reference.

TECHNICAL FIELD

The present invention generally relates to systems and methods for tracking items. More particularly, the present invention relates to systems and methods for tracking items using a sensor device.

BACKGROUND

Asset management has always been an important part of commerce. For example, tracking packages is important to organizations of all kinds, whether it be a company keeping track of inventory to be sold in its stores, or a package delivery provider keeping track of packages being transported through its delivery network. To provide quality service, an organization typically creates and maintains a highly organized network for tracking its packages. Effective management of such networks allows lower cost, reduced delivery time, and enhanced customer service.

In addition to tracking packages, parties that ship and receive packages may also need information regarding the conditions of the packages such as the temperature and humidity of the package. For example, a customer that has ordered a box of wine may want to monitor the temperature of the contents of the box to determine if the temperature and/or humidity goes above or below a set range. Likewise, the party that ships the package may also want to monitor the conditions of the package to ensure that the content arrives in the proper condition.

Technological advances have enabled items to be tracked in ways that far exceed the functionality of a simple list. A rich information framework now can be applied to describe the item's interaction with its surroundings, such as transportation and custodial handcuffs.

Bar codes are one way organizations keep track of items. A retailer, for example, may use bar codes on items in its inventory. For example, items to be sod in a retailer's store may each be labeled with a different bar code. In order to keep track of inventory, the retailer typically scans the bar code on each item. In addition, when an item is sold to a consumer, the bar code for that item is scanned.

Similarly, a package delivery provider may utilize bar codes by associating a bar code with packages to be delivered to a recipient. For example, a package may have a bar code corresponding to a tracking number for that package. Each time the package goes through a checkpoint (e.g., the courier taking initial control of the package, the package being placed in a storage facility, the package being delivered to the recipient, etc.), the package's bar code may be scanned. Bar codes, however, have the disadvantage that personnel must manually scan each bar code on each item in order to effectively track the items.

Radio-frequency identification (RFID) tags are an improvement over typical bar codes. RFID tags do not require manual scanning that is required by typical bar codes. For example, in a retail context, an RFID tag on an inventory item may be able to communicate with an electronic reader that detects items in a shopping cart and adds the cost of each item to a bill for the consumer. RFID tags have also been used to track things such as livestock, railroad cars, trucks, and even airline baggage. These tags typically only avow for basic tracking and do not provide a way to improve asset management using information about the environment in which the items are tracked.

Sensor-based tracking systems are also known which can provide more information than RFID systems. Such systems, however, can be expensive, and may provide extraneous and redundant item information.

Shippers, carriers, recipients, and other parties often wish to know the location, condition, and integrity of shipments before, during, and after transport to satisfy quality control goals, meet regulatory requirements, and optimize business processes. To address these requirements, a system is needed that may monitor data regarding shipments and present this data to a user in real-time or near real-time.

SUMMARY

In one exemplary embodiment, there is provided a device for tracking one or more items. The device may include a plurality of sensors for detecting light, temperature, humidity, pressure, and acceleration. The device may also include a memory for storing information received from the plurality of sensors.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate various embodiments and aspects of the present invention. In the drawings.

DETAILED DESCRIPTION

The following detailed description refers to the accompanying drawings. Wherever possible, the same reference numbers are used in the drawings and the following description to refer to the same or similar parts. While several exemplary embodiments and features are described herein, modifications, adaptations and other implementations are possible, without departing from the spirit and scope of the invention. For example, substitutions, additions or modifications may be made to the components illustrated in the drawings, and the exemplary methods described herein may be modified by substituting, reordering or adding steps to the disclosed methods. Accordingly, the following detailed description does not limit the invention. Instead, the proper scope of the invention is defined by the appended claims.

Device Architecture

Figure 1:
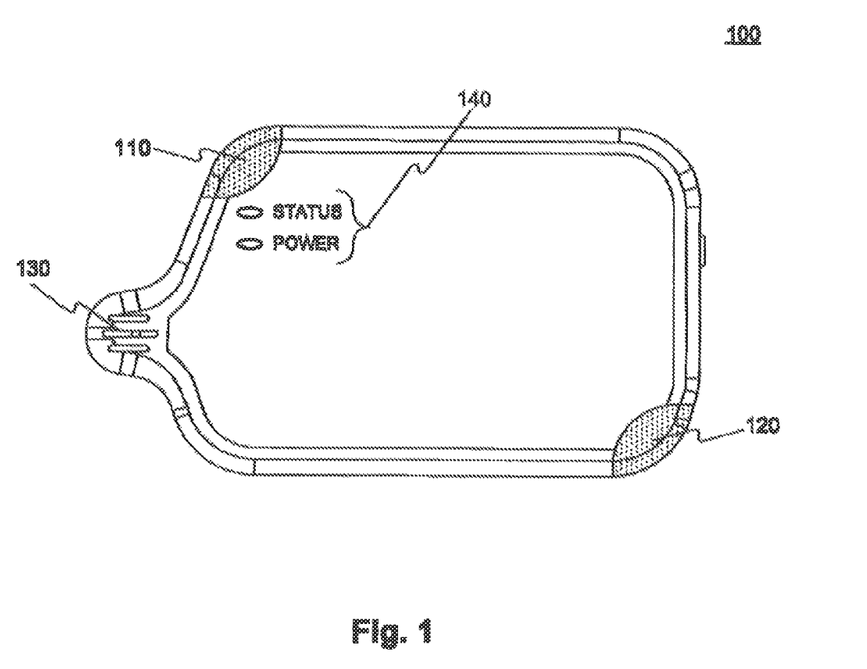
FIG. 1 is a top view of an exemplary sensor device consistent with an embodiment of the present invention.

FIG. 1 illustrates a top view of an exemplary sensor device 100. As depicted in FIG. 1, sensor device 100 may comprise a body that surrounds and protects internal operational components. The body may include a wall formed from a plastic material that permits wireless communications. The wireless communications may, for example, be cellular communications and/or low-power wireless mesh networking communications.

The body of sensor device 100 may be formed from a variety of plastics combinations that may include, for example, metals, metal alloys, plastics, ceramics or a combination of metals, metal alloys, plastics, ceramics. The body may also include an over-molding that surrounds sensor device 100 at the point where the top and bottom housing components come together to create a seam. This aids in providing both a moisture seal and an impact protection guard for the unit.

Figure 4:
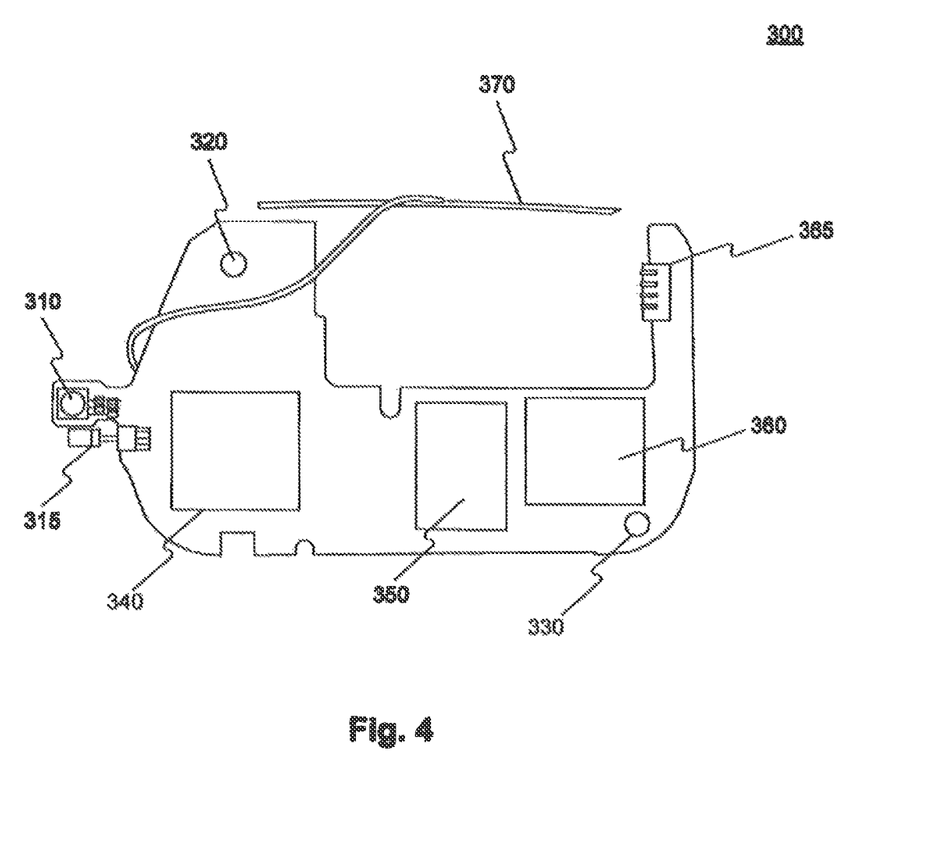
FIG. 4 is a top view of an exemplary circuit board used with a sensor device consistent with an embodiment of the present invention.

Sensor device 100 may also include numerous light sensor lenses. As illustrated in FIG. 1, sensor device 100 may include light sensor lenses 110 and 120. As illustrated in FIG. 4, light sensors 320 and 330 may be covered by light sensor lenses 110 and 120, respectively. Light sensor lenses 110 and 120 may allow light to travel through the lens for detection by light sensors as explained in reference to FIGS. 4 and 5.

Sensor device 100 may be generally rectangular in shape and may include a nose portion on one side. The nose portion may include sensor port 130. Sensor port 130 may include numerous ports that allow the detection of pressure, temperature, and humidity. As illustrated in FIG. 4, sensor 310 and sensor 315 may be covered by sensor port 130 and sensor port 130 may allow pressure, temperature, and humidity to flow through the ports for detection by sensor 310 and sensor 315. For example, temperature and pressure may be detected by sensor 310, and temperature and humidity may be detected by sensor 315. Moreover, a single sensor may detect pressure, temperature, and humidity. Conversely, three sensors may exist and each sensor may detect one of pressure, temperature, and humidity. One of ordinary skill would appreciate that any combination of sensors may be used to detect pressure, temperature, and humidity or any other features as desired.

Figure 5:
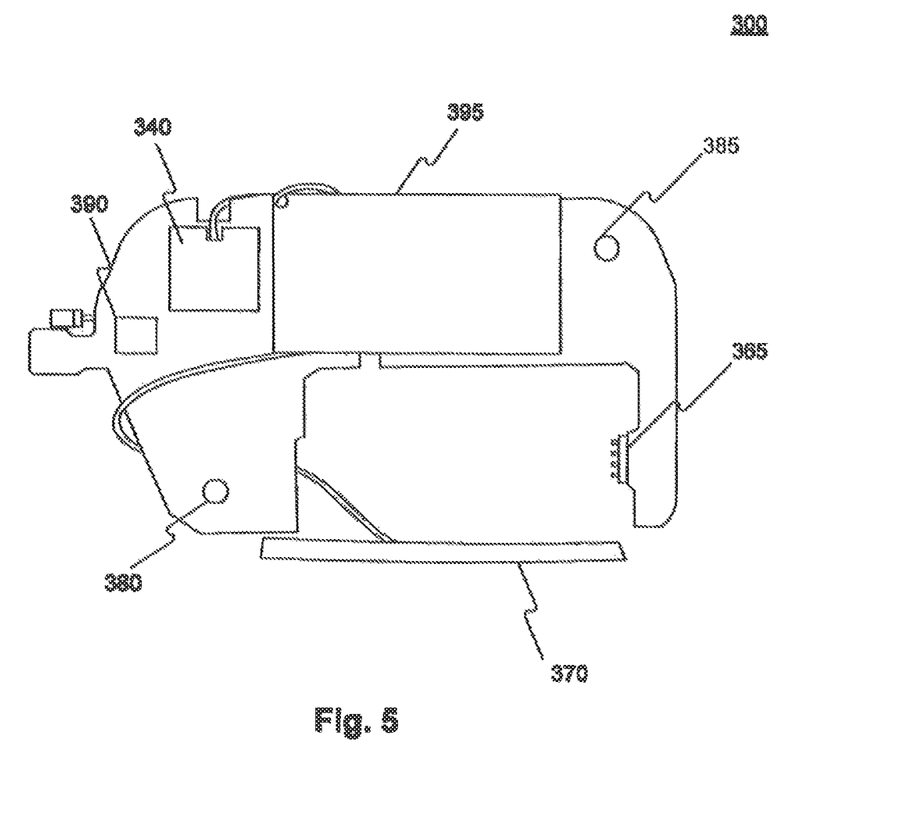
FIG. 5 is a bottom view of an exemplary circuit board used with a sensor device consistent with an embodiment of the present invention.

Sensor port 130 may be placed in the nose portion of sensor device 100 to insulate sensor port 130 from any heat that may be generated from the internal components. Sensor device 100 may include a battery, at least one microcontroller, a global positioning system module, and one or more transceivers as illustrated in FIGS. 4 and 5. When in use, these components may generate heat, and the generated heat may interfere with the readings detected by sensor 310 and sensor 315. Therefore, sensor port 130 may be located within a nose portion of sensor device 100 to minimize or eliminate the effect that the internal components may have on sensor readings.

In addition to locating sensor port 130 in the nose portion of sensor device 100, additional measures may be taken to ensure that any heat from the internal components does not effect sensor readings. For example, within the body of sensor device 100, a wall may exist that acts to separate sensor port 130 from the internal components of sensor device 100 (not shown). For example, the wall may be placed between sensor port 130 and the internal components. The wall may be transparent and may block the heat that is generated by the internal components from reaching sensor port 130. This may help to ensure that sensor 310 and sensor 315 housed within sensor port 130 only detect data external to sensor device 100 and do not detect any heat from the internal components.

Sensor device 100 may also include status and power indicators 140. These indicators may each include a light emitting diode (LED). The LED corresponding to the power indicator may light up when sensor device 100 is in operation. In addition, the LED corresponding to the status indicator may light up during any number of operations including, for example, when sensor device 100 is on, when sensor device 100 is receiving data, or when sensor device 100 is transmitting data. One of ordinary skill would appreciate that a liquid crystal display (LCD), touch screen, or any combination of an LED, LCD, and touch screen may be implemented as status and power indicators 140.

Sensor device 100 may include numerous electrical components that may provide computing operations for sensor device 100. These components may include one or more microprocessors, a flash file system, Read-Only Memory (ROM), Random-Access Memory (RAM), a battery, a circuit board, a wireless modem, a Global Positioning System (GPS) module, and various input/output (I/O) support circuitry. In addition to the above, other circuitry may also include integrated chips for wireless mesh network communications and digital and/or analog sensors.

Figure 2:
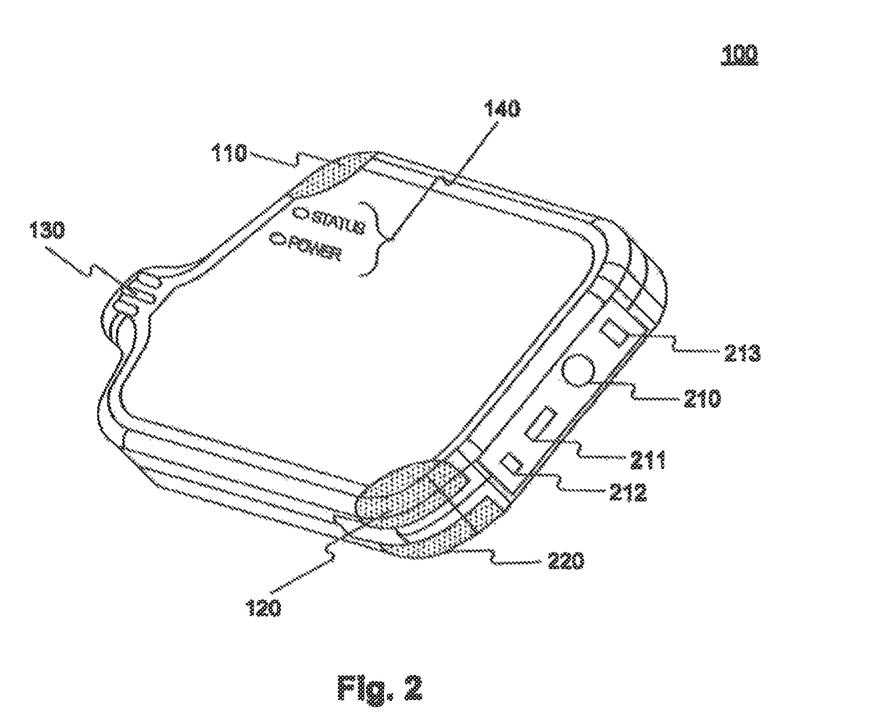
FIG. 2 is a three dimensional view of an exemplary sensor device consistent with an embodiment of the present invention.

FIG. 2 illustrates a three dimensional view of sensor device 100. As depicted in FIG. 2, sensor device 100 may include a power switch 210 that turns sensor device 100 on and off. Power switch 210 may be physically recessed from the body of sensor device 100 to prevent accidental triggering by a user. According to one embodiment, power switch 210 may be spring-loaded and monetarily pressed for on and off operations. According to another embodiment, power switch 210 maybe be pressed and held for a predetermined period of time before an "on" or "off" command is registered with the internal components. This period of time may be any appropriate amount of time such as, for example, five seconds. One of ordinary skill would appreciate that predetermined period of time may be any amount of time that is sufficient to indicate to the internal components that an operator of sensor device 100 is turning the device on or off.

Sensor device 100 may also include a Universal Serial Bus (USB) port 211 for charging sensor device 100. In addition, sensor device 100 may also include external contacts 212 and 213 for charging sensor device 100 via a cradle or other type of external charging device.

Sensor device 100 also includes light sensors lenses 110 and 120. In addition, sensor device 100 may also include light sensor lens 220, which is located on the bottom portion of sensor device 100. FIG. 2 also illustrates sensor port 130. FIG. 2 also illustrates status and power indicators 140.

Figure 3:
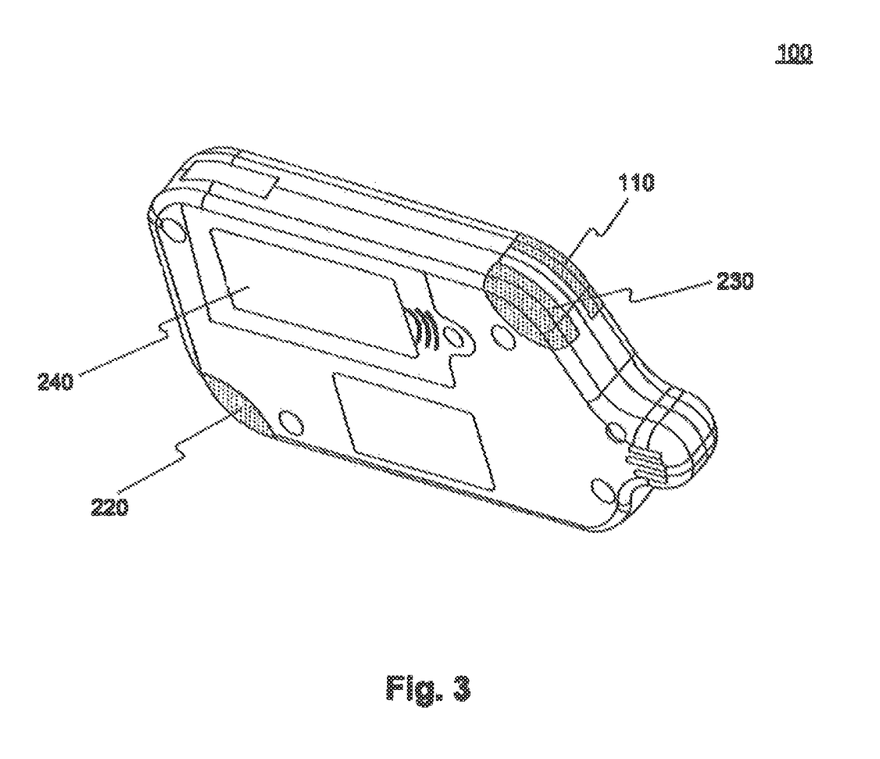
FIG. 3 is a three dimensional view of an exemplary sensor device consistent with an embodiment of the present invention.

FIG. 3 also illustrates a three dimensional view of sensor device 100. As depicted in FIG. 3, sensor device 100 may include light sensor lenses 110 and 220, as previously illustrated, and light sensor lens 230. Sensor device 100 may also include a battery door 240 that may be opened and closed as needed to remove and change the battery. The battery may be any appropriate type of battery including, for example, a rechargeable lithium polymer battery cell.

Accordingly, sensor device 100 may include a total of four light sensor lenses and four corresponding light sensors. One of ordinary skill would appreciate that when sensor device 100 is placed in a package, it may be placed in many different orientations. For example, sensor device 100 may be placed on top of the content of the package. It may also be placed between the content of the package and one of the sides of the package. It may also be placed under the content of the package. Therefore, by including four lights sensors lenses and four light sensors, the location of sensor device 100 within the package is not critical. Sensor device 100 may detect a change in the amount of light within the package regardless of the location of sensor device 100 in comparison to the content of the package. This may result in greater detection of light change and may also eliminate the need for the user of sensor device 100 to place the device in a specific location of the package.

FIG. 4 includes a circuit board 300 of sensor device 100 that contains numerous components. FIG. 4 illustrates a top view of circuit board 300. Circuit board 300 may include sensor 310 and sensor 315. As previously stated, sensor 310 and sensor 315 may be covered by sensor port 130, and sensor port 130 may allow pressure, temperature, and humidity to flow through the ports for detection by sensor 310 and sensor 315. For example, temperature and pressure may be detected by sensor 310, and temperature and humidity may be detected by sensor 315. Moreover, a single sensor may detect pressure, temperature, and humidity. Conversely, three sensors may exist and each sensor may detect one of pressure, temperature, and humidity. One of ordinary skill would appreciate that any combination of sensors may be used to detect pressure, temperature, and humidity or any other features as desired.

Circuit board 300 may also include light sensors 320 and 330. In operation, light sensor lenses 110 and 120 may allow light to pass therethrough. This light is then detected by light sensors 320 and 330. Light sensors 320 and 330 may detect the amount of light within a package that contains sensor device 100 and changes in the amount of light. For example, if the package that contains sensor device 100 is opened, light sensors 320 and 330 may detect a change in the amount of light that indicates that the packages has been opened.

Figure 6:
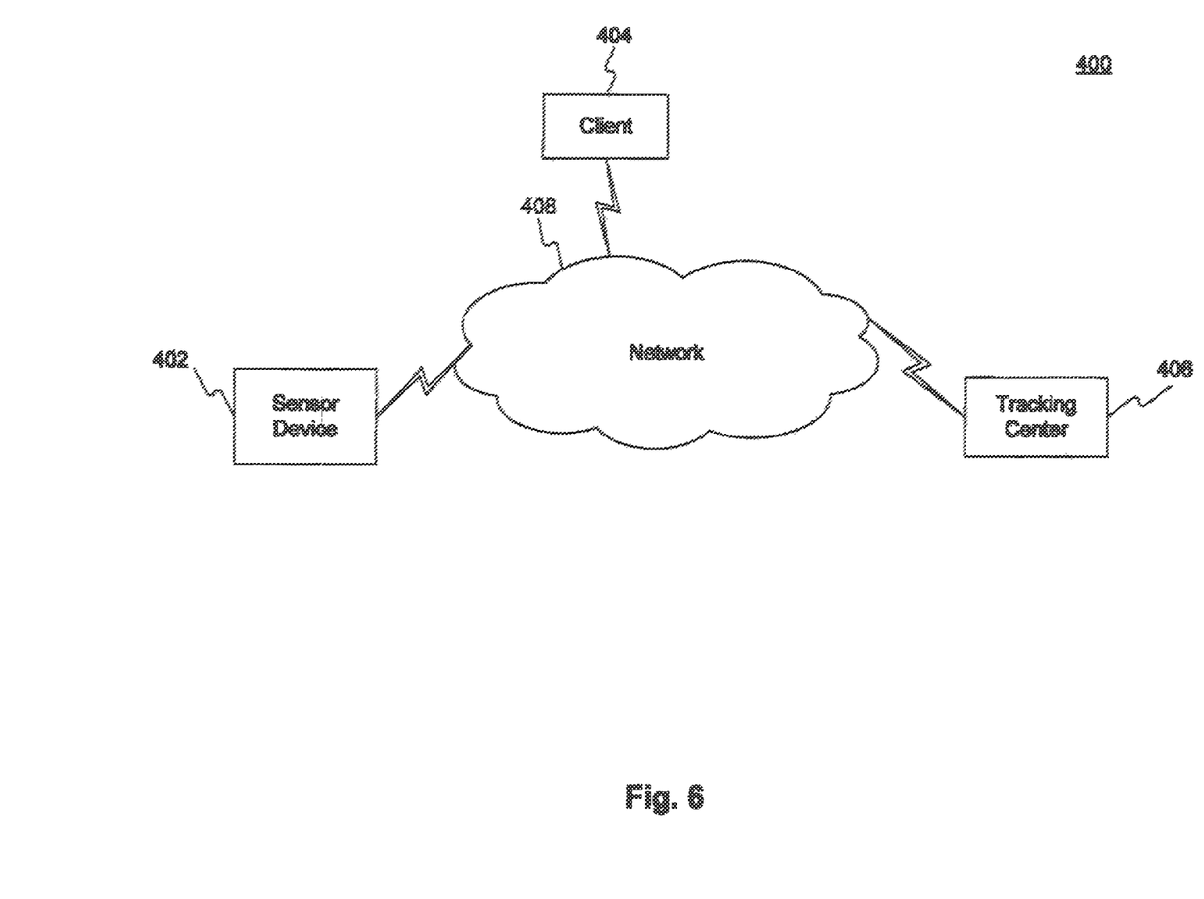
FIG. 6 illustrates an exemplary computing system that can be used to implement embodiments of the invention.

Circuit board 300 may also include a Global Positioning System (GPS) antenna 340, a Subscriber Identity Module (SIM) card 350, and a low-power microprocessor 360. GPS antenna 340 may receive signals from a GPS satellite, and the received signals are used by a GPS module (not shown). The GPS module may be a stand-alone unit or a component of another internal component. SIM card 350 may store the authentication information to allow sensor device 100 to authenticate with network 408, as illustrated in FIG. 6. Low-power microprocessor 360 may be a low-power, wireless module containing a microcontroller. Circuit board 300 may also include a Global System for Mobile (GSM) wireless communications antenna 370.

Circuit board 300 may also include a connector 365. Connector 365 may provide a connection to a battery (not shown) that is placed within sensor device 100. The battery may provide the power for operating the electrical components housed within sensor device 100.

FIG. 5 illustrates a bottom view of circuit board 300. As depicted in FIG. 5, circuit board 300 may also include light sensors 380 and 385. In addition, circuit board 300 may also include accelerometer 390. Accelerometer 390 may detect a change in the velocity of sensor device 100. For example, if sensor device 100 is located in a package, and the package is located in a parked car, accelerometer 390 would not detect a change in velocity. However, when the car starts moving, accelerometer 390 would sense the corresponding change in velocity.

Circuit board 300 may also include a high-power microprocessor 395 that may be a high-power, wireless module containing a microcontroller. High-power microprocessor 395 may store the pressure, temperature, humidity, and acceleration data that is detected by sensor 310, sensor 315, and accelerometer 390. In addition, high-power microprocessor 395 may also store data regarding light detected by light sensors 320 and 330. Moreover, high-power microprocessor 395 may also store the data regarding light detected by light sensors 380 and 385.

As illustrated in FIGS. 4 and 5, circuit board 300 may include seven sensors 310, 315, 320, 330, 380, 385, and 390. According to one embodiment, light sensor 320 is located on the top portion of circuit board 300 and light sensor 380 is located directly underneath light sensor 320 and on the bottom portion of circuit board 300. Moreover, light sensor 330 is located on the top portion of circuit board 300 and light sensor 385 is located directly underneath light sensor 330 and on the bottom portion of circuit board 300. One of ordinary skill would appreciate that light sensors 320, 330, 380, and 385 may be located in any desired area of circuit board 300. For example, light sensors 320, 330, 380, and 385 may be each located on the top portion of circuit board 300 or the bottom portion of circuit board 300.

According to the above embodiment, the location of light sensors 320, 330, 380, and 385 may provide for optimal light detection. According to this embodiment, sensor device 100 thus includes four light sensor lenses 110, 120, 220, and 230 respectively connecting to sensors 320, 330, 385, and 380. This provides for accurate detection of changes in the amount of light in the package that houses sensor device 100. As previously stated, sensor device 100 may be placed in a plurality of locations within the package. It may also be placed between the content of the package and one of the sides of the package. It may also be placed under the content of the package. Therefore, by including four lights sensors lenses and four corresponding light sensors, the location of sensor device 100 within the package is not critical. Because sensor device 100 includes four light sensors lenses and four light sensors, sensor device 100 may detect a change in the amount of light within the package regardless of the location of sensor device 100 in comparison to the content of the package. This may result in greater detection of light change and may also eliminate the need for the user of sensor device 100 to place the device in a specific location of the package.

In operation, when sensor device 100 is turned on by pressing power switch 210, light sensors 320, 330, 380, and 385 may begin to sense a changes in light based, in accordance with a user configuration. In addition, sensor 310 may begin to sense a change in temperature and/or pressure, sensor 315 may begin to sense a change in temperature and/or humidity, and accelerometer 390 may begin to sense acceleration. A user of sensor device 100 may program sensor device 100 to detect data hourly, daily, or at any other interval. For example, a user may configure sensor device 100 to detect data at any set interval.

As depicted in FIGS. 4 and 5, low-power microprocessor 360 and high-power microprocessor 395 are located on opposite sides of circuit board 300. One of ordinary skill would appreciate that low-power microprocessor 360 and high-power microprocessor 395 may be located in any desired location on circuit board 300. High-power microprocessor 395 may be viewed as a master processor and low-power microprocessor 360 may be viewed as a slave processor. Microprocessors 360 and 395 are coupled together in a master/slave relationship whereby control of sensor device 100 may be shared between the two processors.

Microprocessors 360 and 395 may work together to operate sensor device 100 based on the configuration data. High-power microprocessor 395 may control high power functions of sensor device. These functions may include network connectivity, transmitting and/or receiving, persistent storage of recorded data, location data collection (e.g. GPS), high-level power management, and electronics diagnostics that may consume power resources. Low-power microprocessor 360 may control lower power functions. These functions may include sensor data collection, low-level power management, and low-power mesh networking transmitting and/or receiving. By way of example, an ultra, low-level power management solution may involve shutting down the master (high-power) processor. In this case, a well-defined relationship is in place to ensure that smooth transitions occur as management decisions are passed back and forth between microprocessors 360 and 395.

In addition, an Application Protocol Interface (API) may be used to simplify the interaction between the master microprocessor 395 and slave microprocessor 360 and to aid in the sharing of data generated in or received by sensor 100. This API may be binary in nature and may have two main parts including, for example a header and a payload of data. The API header may consist of, for example, length, sequence, source, destination, and type data. The payload may be a flexible message that depends on what was captured at a point in time during operation of sensor device 100.

The internal components of sensor device 100 may also include subassemblies for processing, transmitting and/or receiving wireless signals (e.g. transmitter, receiver, and antenna). According to one embodiment, sensor device 100 may support modules for two wireless protocols (not shown). These protocols may support Global System for Mobile (GSM) wireless communications in the range of about 850 to about 1900 MHz and low-power mesh networking in the 2.4 GHz range. One module may located on top of circuit board 300 and the other may located on the bottom of circuit board 300. One of ordinary skill would appreciate that the location of the support modules may be modified. Both modules may be operatively coupled to circuit board 300 and its various components. Although not shown, sensor device 100 may also include components for supporting Bluetooth, WiFi, and ZigBee communication.

Sensor device 100 is configured according to operation need. By way of example, the sensor device 100 may be configured to collect environmental, security and/or location-based data continuously or at desired intervals. Configuration of data collection and/or reporting may have a direct impact on sensor device 100 power management. For example, there may be operational trade-offs depending on how sensor device 100 is configured, location-based (GPS) services, and other points of interest. Once sensor device 100 receives an operating scenario (e.g. from tracking center 406 in FIG. 6), sensor device 100 may be associated with a package for tracking. Sensor device 100 may transmit data to a host system (e.g. tracking center 406 in FIG. 6). If sensor device 100 cannot establish a wireless network connection, sensor device 100 may record the data to persistent storage in, for example, memory of high-power microprocessor 395. Once a wireless connection is established, the recorded data is transmitted to tracking center 406 and may be removed from storage. This repetitive pattern is followed until tracking of the package is complete. For example, sensor device 100 may choose to turn itself off when tracking is completed.

Sensor device 100 may also be configured to minimize the overall power usage to extend the battery life of the device. For example, if sensor device 100 is placed in a package that will be stored in a warehouse for several weeks before shipment, it is important that sensor device 100 has the ability to provide data to tracking center 406 for an extended period of time. Therefore, sensor device 100 may be configured to turn off any combination of the GPS antenna 340, SIM card 350, low-power microprocessor 360, GSM antenna 370, and high-power microprocessor 395 to extend the battery life.

According to the above example, sensor device 100 may turn off GPS antenna 340, SIM card 350, GSM antenna 370, and high-power microprocessor 395. Even though these elements are off, sensor device 100 may continue to sense changes in, for example, light, temperature, pressure, humidity, and/or acceleration, and sensor device 100 may continue to report this information at predetermined intervals to low-power microcontroller 360. If an event occurs, such as sensor device 100 begins to move, accelerometer 390 may sense this change, report the information to low-power microcontroller 360, and sensor device 100 may selectively turn on one or more of the elements that were previously turned off. Likewise, sensor device 100 may selectively turn on one or more of the elements that were previously turned off based on a change in light, temperature, pressure, and/or humidity.

Computing System

By way of a non-limiting example, FIG. 6 illustrates a system 400 in which the features and principles of the present invention may be implemented. The number of components in system 400 is not limited to what is shown and other variations in the number of arrangements of components are possible, consistent with embodiments of the invention. The components of FIG. 4 may be implemented through hardware, software, and/or firmware. System 400 may include a sensor device 402 (which corresponds to sensor device 100 in FIG. 1), a client 404, a tracking center 406, and a network 408.

Network 408 provides communications between the various entities depicted in system 400. Network 408 may be a shared, public, or private network and encompass a wide area or local area. Network 408 may be implemented through any suitable combination of wired and/or wireless communication networks (including Wi-Fi networks, GSM/GPRS networks, TDMA networks, CDMA networks, Bluetooth networks, or any other wireless networks). By way of example, network 408 be implemented through a wide area network (WAN), local area network (LAN), an intranet and/or the Internet. Further, the entities of system 400 may be connected to multiple networks 408, such as, for example, to a wireless carrier network, a private data network and the public Internet.

Sensor device 402 may be a device for use in tracking various items, and may be attached to or included in the items that are to be tracked. For example, sensor device 402 may be attached to or enclosed in a package that is being sent to a recipient using a delivery service such as Federal Express Corporation, ("FedEx"). Alternatively, sensor device 402 may be attached to or enclosed in a container holding inventory being delivered to a retailer. The aforementioned items are exemplary and may comprise any deliverable elements.

Sensor device 402 may store information associated with an item tracking number for a corresponding item. The item tracking number may be a FedEx tracking number or similar tracking number. In one embodiment, sensor device 402 may be capable of measuring or detecting one or more conditions such as location, temperature, acceleration, light level, motion, pressure, humidity, gas level, airflow, vibrations, or other environmental conditions. Sensor device 402 may also have the ability to directly transmit and receive information to/from tracking center 406 via network 408 (e.g., using known wireless communications means).

Tracking center 406 may provide a platform for tracking items being delivered to a recipient. Tracking center 406 may be implemented using a combination of hardware, software, and/or firmware, and may be operable to receive and store sensor data from sensor device 402. For example, sensor device 402 may periodically send tracking center 406 sensor data reflecting conditions measured or detected by sensor device 402. Such sensor data may include location, temperature, acceleration, light level, motion, pressure, humidity, gas level, airflow, vibrations, or other environmental conditions.

Tracking center 406 is also operable to respond to requests for sensor data. For example, a customer may use client 404 to enter a request for sensor data stored at tracking center 406. The request may include one or more triggering parameters, which can be used to find the requested sensor data. Exemplary triggering parameters may include a sensor identification number, item tracking number, location, temperature, acceleration, light level, humidity, pressure, gas level, airflow, vibrations, etc. Accordingly, by way of example, a customer may request temperature measurements within a certain range of a specific location. The distance from the specific location is the triggering parameter in that case.

When tracking center 406 receives a request for sensor data from a client 408, tracking center 406 may search a database resident at tracking center 406 and return the requested sensor data, if found. Access to the sensor data may be managed or open. For example, if access is managed, client 408 and/or the customer would need to be authenticated before sensor data is made available to client 408 and/or the customer. In addition to or instead of searching a database for sensor data, tracking center 406 may request sensor data directly from sensor device 402.

Tracking center 406 may also provide updated and/or new programming to provide configuration of sensor device 402. For example, programming may specify the manner in which a device senses environmental conditions. Programming of sensor device 402 may be altered, for example, by storing new or modified instructions in a memory (not shown) located in sensor device 402. Programming changes may be made arbitrarily (e.g., at the discretion of a programmer) or in response to a detected condition. For example, suppose sensor device 402 detects a temperature above a predetermined level. When sensor device 402 reports the temperature to tracking center 406, an alarm or alert may be triggered to bring this information to the attention of personnel associated with tracking center 406. Tracking center 406, in turn, may alter the programming of sensor device 402 to check the temperature more frequently. One of ordinary skill in the art will appreciate that other parameters can be used as the basis for altering programming.

Moreover, sensor device 402 may be preconfigured to determine programming changes without receiving instructions from tracking center 406. For example, if sensor device 402 determines that the temperature of the device has reached a predetermined threshold, sensor device 402 may change the reporting frequency without first contacting tracking center 406 to receive a programming change to alter the reporting frequency.

Client 404 provides users with an interface to network 408. By way of example, client 404 may be implemented using any device capable of accessing a data network, such as a general purpose computer or personal computer equipped with a modem or other network interface. Client 404 may also be implemented in other devices, such as a Blackberry™, Ergo Audrey™, mobile phones (with data access functions), Personal Digital Assistant ("PDA") with a network connection, IP telephony phone, or generally any device capable of communicating over a data network.

Client 404 may be utilized by users to request sensor data from tracking center 406. For example, a user may subscribe to a service that allows the user to access up-to-date information about one or more sensors. Alternatively, a subscription to a service is not necessary to access the information. In order to request sensor data, the user may enter information on client 404 indicative of the desired sensor data. For example, the user may enter information requesting the current location and temperature of all sensors within a certain radius of a specified sensor. After the customer enters this information, client 404 may send a request to tracking center 104, which in turn may search its database or request the information directly from the sensors. When tracking center 406 finds the requested information, it may send the information back to client 404. As illustrated in FIG. 4, one sensor device 402 and one client 406 may be connected to network 408. However, one of ordinary skill would appreciate that more than one sensor device and more than one client may be connected to network 408.

Flowchart

Figure 7:
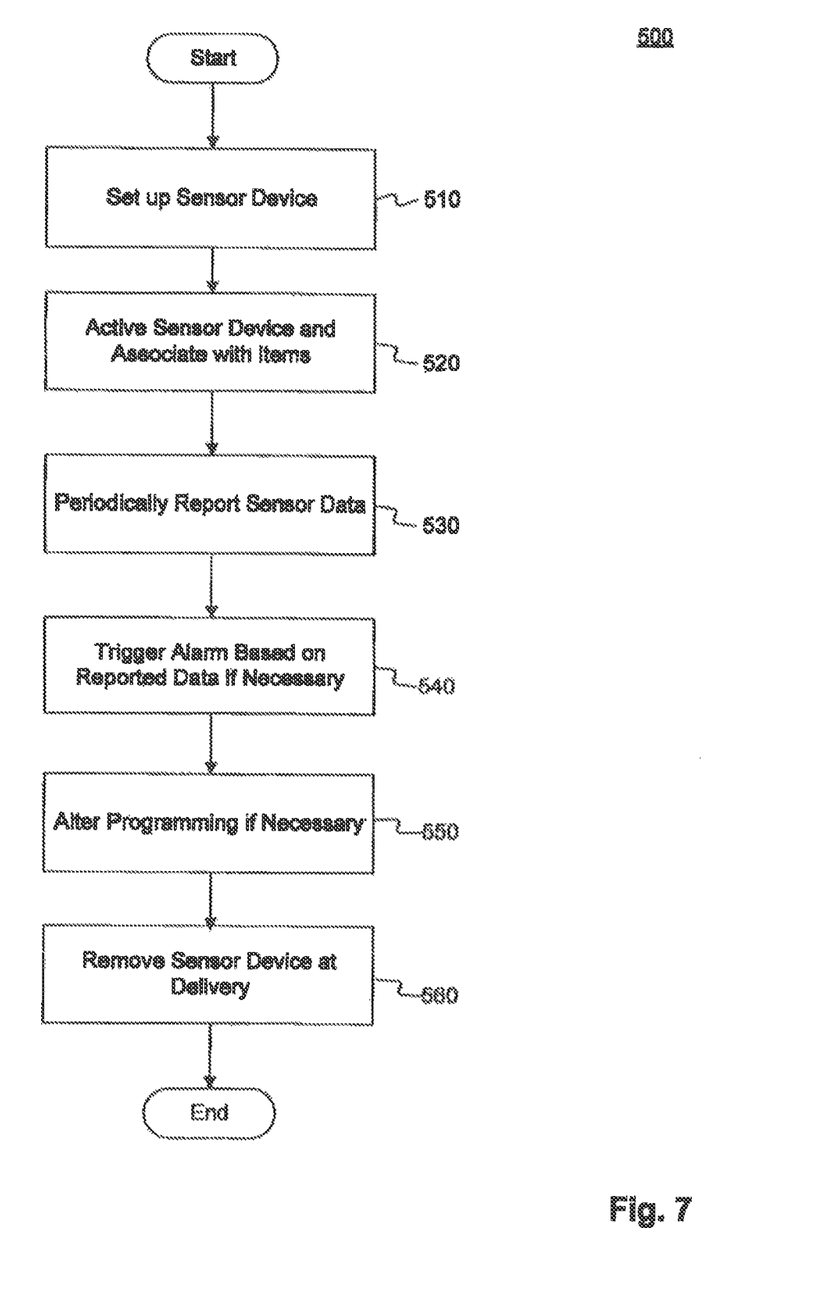
FIG. 7 illustrates a flowchart of an exemplary method for tracking items consistent with an embodiment of the present invention.

FIG. 7 illustrates a flowchart 500 of an exemplary method for tracking items, consistent with the principles of the present invention. Although the steps of the flowchart are described in a particular order, one skilled in the art will appreciate that these steps may be performed in a modified or different order, or that certain steps may be omitted. Further, one or more of the steps in FIG. 7 may be performed concurrently or in parallel.

Sensor device 100 is configured based on the requirements of a shipper (step 510). For example, a party may require specific programming (specifying, for example, the manner in which a device detects environmental conditions) for sensor device 100 are to be associated with items to be sent to recipients. Alternatively, sensor device 100 may be configured based on default programming. A shipper who desires to send an item to a recipient may purchase or otherwise acquire sensor device 100 to be attached to or placed in an item to be shipped. A shipper, for example, may be an item delivery company such as FedEx, a retailer, or a manufacturer that makes its own deliveries. One of ordinary skill in the art will appreciate that it is possible that the customer and the shipper are the same entity.

Sensor device 100 may be activated and associated with the item(s) being shipped (step 520). For example, a courier or other employee of the shipper may turn sensor device 100 on and place it in or attach it to packaging associated with a corresponding item. The courier or other employee may also associate sensor device 100 with an item tracking number. For example, the courier or other employee may cause information to be stored at tracking center 104 that specifies that the item tracking number is currently assigned to an identification number for the item tracking device. Alternatively, no item tracking number is associated with sensor device 100.

As noted above with reference to FIGS. 2-5, sensor device 100 may include a plurality of sensors that measure or detect one or more conditions such as location, temperature, light level, motion, pressure, humidity, gas level, airflow, vibrations, or other environmental conditions. Sensor device 100 that includes such sensors periodically report sensor data to tracking center 104 (step 530).

When tracking center 406 receives sensor data, if that data is indicative of a predetermined condition, tracking center 406 may trigger an appropriate alarm (step 540). For example, suppose sensor device 100 detects a temperature above a certain level. When sensor device 100 reports the temperature level to tracking center 406, an alarm or alert may be triggered to bring this information to the attention of personnel associated with tracking center 406. Personnel may then monitor the situation more closely or take another appropriate action. Alternatively or additionally, the pertinent courier or other party may be notified of the alarm condition via sensor device 100.

Tracking center 406 may also alter the programming of sensor device 100 if necessary or desired (step 550). In the example of sensor device 100 detecting a temperature above a certain level, tracking center 406 may, in turn, alter the programming of sensor device 100 to check the temperature more frequently. Alternatively, sensor device 100 may be preconfigured to determine programming changes without receiving instructions from tracking center 406. For example, if sensor device 100 determines that the temperature of the device has reached a predetermined threshold, sensor device 100 may change the reporting frequency without first contacting tracking center 406 to receive a programming change to alter the reporting frequency.

One of ordinary skill in the art will appreciate that other parameters can be used as the basis for altering programming. Moreover, one of ordinary skill in the art will appreciate that programming may be altered for reasons other than the detection of predetermined conditions, and that the programming of the aforementioned devices may be altered without the intervention of tracking center 406.

Finally, when an item reaches its final destination (e.g., delivered to the recipient), the courier removes and may deactivate sensor device 100 (step 560).

While certain features and embodiments of the invention have been described, other embodiments of the invention will be apparent to those skilled in the art from consideration of the specification and practice of the embodiments of the invention disclosed herein. Furthermore, although embodiments of the present invention have been described as being associated with data stored in memory and other storage mediums, one skilled in the art will appreciate that these aspects can also be stored on or read from other types of computer-readable media, such as secondary storage devices, like hard disks, floppy disks, or a CD-ROM, or other forms of RAM or ROM. Further, the steps of the disclosed methods may be modified in various ways, including by reordering steps and/or inserting or deleting steps, without departing from the principles of the invention.

Several different embodiment of sensor device 100 may exist. For example, although one embodiment includes a wireless module that combines GPS and GSM technologies, the two may be separated within the sensor device 100 or not included. In addition, the above embodiments may also apply to other electronic devices such as RFID tags, smart dust motes, smart phones, and accessories for these devices.

It is intended, therefore, that the specification and examples be considered as exemplary only, with a true scope and spirit of the invention being indicated by the following claims and their full scope of equivalents.

What is claimed is:

1. A package tracking device, comprising:
 a battery;
 at least two light sensors configured to detect changes in an amount of light within the package;
 a circuit board arranged with a first processing device associated with a first plurality of functions of the device, wherein the first plurality of functions includes collecting data from the at least two light sensors, and a second processing device associated with a second plurality of functions of the device, wherein power requirements of functions from the second plurality of functions exceed power requirements of functions from the first plurality of functions;
 the device is configured to:
  turn off any combination of elements associated with functions from the first plurality of functions and the second plurality of functions to minimize the overall power usage; and
 selectively turn on one or more of the elements that were previously turned off, upon detection of a change in the amount of light within the package.

2. The package tracking device of claim 1, wherein the combination of elements includes one or more of the following: the first processing device, the second processing device, a GPS antenna, a GSM antenna, and a SIM card.

3. The package tracking de vice of claim 1, wherein the first plurality of functions further includes low-level power management, low-power mesh networking transmitting, and low-power mesh networking transmitting receiving.

4. The package tracking device of claim 1, wherein the second plurality of functions includes network connectivity, data transmitting, data receiving, persistent storage of recorded data, location data collection, high-level power management, and electronics diagnostics.

5. The package tracking device of claim 1, wherein the first processing device and the second processing device are located on opposite sides of the circuit board.

6. The package tracking device of claim 1, further configured to detect the change in the amount of light within the package when the combination of elements is off.

7. The package tracking device of claim 1, further configured to detect a change in the amount of light within the package regardless of a position of the device in the package.

8. The package tracking device of claim 1, further including a set of sensors configured to detect changes of at least one of the following: temperature, acceleration, light level, motion, pressure, humidity, gas level, airflow, and vibrations.

9. The package tracking device of claim 8, wherein when a change in one of the set of sensors is above a predetermined threshold, the package tracking device changes a parameter associated with a function from the first plurality of functions.

10. A package tracking device, comprising:
 a battery;
 a set of sensors configured to detect one or more conditions of the package, wherein the set of sensors includes at least two light sensors;
 a circuit board arranged with:

a first processing device associated with a first plurality of functions of the device, wherein the first plurality of functions includes collecting data from the set of sensors and detecting a change in light and selectively turn on one or more of the elements that were previously turned off, and a second processing device associated with a second plurality of functions of the device, wherein power requirements of functions from the second plurality of functions exceed power requirements of functions from the first plurality of functions; and wherein the device is configured to turn off any combination of elements associated with functions from the second plurality of functions to minimize the overall power usage and to extend the battery life.

11. The package tracking device of claim 10, wherein the one or more conditions includes temperature, acceleration, light level, motion, pressure, humidity, gas level, airflow, and vibrations.

12. The package tracking device of claim 10, wherein the combination of elements includes one or more of the following: the first processing device, the second processing device, a GPS antenna, a GSM antenna, and a SIM card.

13. The package tracking device of claim 10, wherein the first plurality of functions further includes low-level power management, low-power mesh networking transmitting, and low-power mesh networking transmitting receiving.

14. The package tracking device of claim 10, wherein the second plurality of functions includes network connectivity, data transmitting, data receiving, persistent storage of recorded data, location data collection, high-level power management, and electronics diagnostics.

15. The package tracking device of claim 10, wherein the first processing device and the second processing device are located on opposite sides of a circuit board.

16. The package tracking device of claim 10, wherein the set of sensors configured to detect changes when the combination of elements is off.

17. The package tracking device of claim 10, wherein the set of sensors includes at least an accelerometer, and the first processing device is configured to detect a change in acceleration and selectively turn on one or more of the elements that were previously turned off.

18. The package tracking device of claim 10, wherein the set of sensors includes at least two light sensors, and the first processing device configured to detect a change in light and selectively turn on one or more of the elements that were previously turned off.

19. The package tracking device of claim 10, wherein the first processing device configured to detect a change in pressure and selectively turn on one or more of the elements that were previously turned off.

20. The package tracking device of claim 10, wherein the first processing device configured to detect a change in humidity and selectively turn on one or more of the elements that were previously turned off.

* * * * *

UNITED STATES PATENT AND TRADEMARK OFFICE
CERTIFICATE OF CORRECTION

PATENT NO. : 9,720,480 B2  
APPLICATION NO. : 14/638577  
DATED : August 1, 2017  
INVENTOR(S) : Timothy L. Gregory et al.

Page 1 of 1

It is certified that error appears in the above-identified patent and that said Letters Patent is hereby corrected as shown below:

In Claim 3, Column 12, Line 33:
"tracking de vice" should read --tracking device--.

In Claim 10, Column 13, Lines 4-5:
"selectively turn on" should read --selectively turning on--.

In Claim 16, Column 14, Line 8:
"set of sensors configured" should read --set of sensors is configured--.

In Claim 18, Column 14, Line 17:
"device configured" should read --device is configured--.

In Claim 19, Column 14, Line 21:
"device configured" should read --device is configured--.

In Claim 20, Column 14, Line 25:
"device configured" should read --device is configured--.

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*